United States Patent
Brehme et al.

(10) Patent No.: US 8,252,934 B2
(45) Date of Patent: Aug. 28, 2012

(54) PROCESS FOR THE PREPARATION OF 4-AMINO-2,2,6,6-TETRAMETHYLPIPERIDINE

(75) Inventors: Volker Brehme, Nottuln-Appelhuelsen (DE); Daniel Dembkowski, Essen (DE)

(73) Assignee: Evonik Degussa GmbH, Essen (DE)

( * ) Notice: Subject to any disclaimer, the term of this patent is extended or adjusted under 35 U.S.C. 154(b) by 432 days.

(21) Appl. No.: 12/362,136

(22) Filed: Jan. 29, 2009

(65) Prior Publication Data

US 2009/0209766 A1  Aug. 20, 2009

(30) Foreign Application Priority Data

Feb. 1, 2008  (DE) .................. 10 2008 000 214
Jul. 1, 2008   (DE) .................. 10 2008 040 045

(51) Int. Cl.
*C07D 211/00* (2006.01)
*C07D 211/56* (2006.01)

(52) U.S. Cl. ........................ 546/184; 546/244

(58) Field of Classification Search .............. 546/184, 546/244

See application file for complete search history.

(56) References Cited

U.S. PATENT DOCUMENTS

| | | | |
|---|---|---|---|
| 4,429,157 A | 1/1984 | Disteldorf et al. |
| 5,693,817 A | 12/1997 | Frentzen et al. |
| 5,773,622 A | 6/1998 | Jegelka et al. |
| 5,945,536 A | 8/1999 | Jegelka et al. |
| 2008/0251758 A1 | 10/2008 | Kirchhoff et al. |

FOREIGN PATENT DOCUMENTS

| EP | 0 042 119 | 12/1981 |
|---|---|---|
| SU | 1088304 A | * 11/1987 |

OTHER PUBLICATIONS

U.S. Appl. No. 06/231,358, filed Apr. 2, 1981, Broschinski, et al.

* cited by examiner

*Primary Examiner* — Susannah Chung
(74) *Attorney, Agent, or Firm* — Oblon, Spivak, McClelland, Maier & Neustadt, L.L.P.

(57) ABSTRACT

4-amino-2,2,6,6-tetramethylpiperidine is prepared by reacting 2,2,6,6-tetramethylpiperidine-4-one with ammonia and hydrogen in the presence of nickel and/or cobalt catalyst and water. The main reaction is carried out at a pressure of at most 50 bar and a temperature of at most 120° C. up to a conversion of the 2,2,6,6-tetramethylpiperidine-4-one of at least 80%. Then, an after-reaction takes place at a higher temperature and at a higher pressure compared to the pressure and temperature of the main reaction.

20 Claims, No Drawings

PROCESS FOR THE PREPARATION OF 4-AMINO-2,2,6,6-TETRAMETHYLPIPERIDINE

BACKGROUND OF THE INVENTION

1. Field of the Invention

The present invention relates to a process for the preparation of 4-amino-2,2,6,6-tetramethylpiperidine (TAD) from 2,2,6,6-tetramethylpiperidine-4-one (triacetonamine, TAA), ammonia and hydrogen in the presence of a catalyst.

2. Discussion of the Background

4-Amino-2,2,6,6-tetramethylpiperidine is referred to as sterically hindered on account of the 2,2,6,6-substitution and can be used widely, in particular as intermediate in the production of UV stabilizers for polymers. It is important here that besides having a high chemical purity, the 4-amino-2,2, 6,6-tetramethylpiperidine has no or the lowest possible intrinsic color. Even over a prolonged storage period of several months, no discoloration of the 4-amino-2,2,6,6-tetramethylpiperidine should take place. This is particularly critical when the 4-amino-2,2,6,6-tetramethylpiperidine is used for producing stabilizers or directly as additive since the product quality of the 4-amino-2,2,6,6-tetramethylpiperidine has a decisive influence on the quality of the stabilized polymers.

4-Amino-2,2,6,6-tetramethylpiperidine is generally prepared by a reductive amination of 2,2,6,6-tetramethylpiperidine-4-one in one or two stages in the presence of catalysts.

Thus, EP 0 776 887 A1 describes a continuous process at pressures of from 285 to 300 bar in the presence of metal catalysts selected from cobalt, nickel, ruthenium, palladium and platinum, and in the absence of solvents. The process according to DE 30 03 843 A1 is likewise carried out at pressures above 200 bar and without solvents and can also be carried out as a discontinuous process.

However, discontinuous processes are generally carried out at a lower pressure and in the presence of catalysts which have cobalt or nickel. Thus, EP 0 714 890 A2 describes a process at a pressure of 95 bar and likewise without solvents. Here, the 4-amino-2,2,6,6-tetramethylpiperidine is obtained in a purity of from 95 to 97%.

Often, however, processes are described which are carried out in the presence of solvents, such as, for example, water or alcohols. Thus, GB 2 176 473 and CN 1358713 A describe a process using water as solvent and in the presence of alkali metal and alkaline earth metals as cocatalyst at a pressure of from 10 to 30 bar. The yields attained are in the case of GB 2 176 473 90 to 95%, and in the case of CN 1358713 A 96.6%.

Li Yang et al. in Chemical Industry and Engineering Vol. 23 No. 4, 323-327 describe the influence of a number of process parameters on the process for the preparation of 4-amino-2, 2,6,6-tetramethylpiperidine. Thus, Li Yang et al. describe that the selectivity can be increased through the use of cobalt catalysts instead of nickel catalysts. The suitable temperature is 90 to 100° C. and the hydrogen pressure should be 15 to 25 bar. As is also the case in the background art described above, options to improve the color stability of the 4-amino-2,2,6,6-tetramethylpiperidine are not described.

By contrast, WO 99/16749 describes a process for the purification of 2,2,6,6-tetrasubstituted 4-aminopiperidines in order to improve the color stability of these compounds. After the distillation of the 2,2,6,6-tetrasubstituted 4-aminopiperidine, this is reacted with hydrogen in the presence of a hydrogenation or dehydrogenation catalyst and separated off from the reaction mixture. Using this purification step, the APHA color number can be lowered to less than 10.

WO 97/46529 also describes a process for the purification of these piperidines. In this process, water and high-boiling compounds are firstly removed from the reaction mixture by distillation, a reducing agent is added and, finally, the piperidine is isolated by distillation. By adding a reducing agent, in particular $NaBH_4$, the APHA color number can be lowered to less than 15.

The two PCT publications mentioned in the previous paragraphs each describe an additional purification step in order to achieve the desired color stability.

SUMMARY OF THE INVENTION

It was therefore the object of the present invention to provide a process at medium pressure for the preparation of 4-amino-2,2,6,6-tetramethylpiperidine which permits the preparation of color-stable 4-amino-2,2,6,6-tetramethylpiperidine with an APHA value of <20 for a storage time of 6 months.

This and other objects have been achieved by the present invention, the first embodiment of which includes a process for the preparation of 4-amino-2,2,6,6-tetramethylpiperidine, comprising:

reacting 2,2,6,6-tetramethylpiperidine-4-one with ammonia and hydrogen in the presence of a nickel and/or cobalt catalyst, and water, wherein a main reaction is carried out at a pressure of at most 50 bar and a temperature of at most 120° C. up to a conversion of the 2,2,6,6-tetramethylpiperidine-4-one of at least 80%, and then an after-reaction takes place at a higher temperature and at a higher pressure compared to the pressure and temperature of the main reaction.

DETAILED DESCRIPTION OF THE INVENTION

Surprisingly, a process for the preparation of 4-amino-2,2, 6,6-tetramethylpiperidine with a high color stability has been found which is characterized in that, after the main reaction, an after-reaction takes place at a higher temperature and at a higher pressure compared to the pressure and temperature of the main reaction. In this way, it is surprisingly possible to prepare 4-amino-2,2,6,6-tetramethylpiperidine with a high color stability which is retained even after a storage time of six months at room temperature. Compared with the background art, this process has the advantage that the downstream after-reaction can take place in the same reactor without interconnected process steps. Furthermore, during this after-reaction, no additional additives, for example reducing agents such as $NaBH_4$, have to be added. In this way, the main reaction can be carried out under surprisingly mild conditions and the formation of 4-hydroxy-2,2,6,6-tetramethylpiperidine can be suppressed. Since the after-reaction can be carried out without the further addition of additives and/or upstream process steps, this process represents an economically interesting process variant at medium pressure in order to prepare 4-amino-2,2,6,6-tetramethylpiperidine with a high color stability.

The invention thus provides a process for the preparation of 4-amino-2,2,6,6-tetramethylpiperidine by reacting 2,2,6,6-tetramethylpiperidine-4-one with ammonia and hydrogen in the presence of nickel or cobalt catalysts and water, characterized in that the main reaction is carried out at a pressure of at most 50 bar and a temperature of at most 120° C. up to a conversion of the 2,2,6,6-tetramethylpiperidine-4-one of at least 80% and then an after-reaction takes place at a higher temperature and at a higher pressure compared to the pressure and temperature of the main reaction.

The measurement of the color stability of the 4-amino-2, 2,6,6-tetramethylpiperidine prepared by the process according to the invention is carried out by ascertaining the APHA color number in accordance with EN ISO 6271. The APHA color number is measured using a 20% strength by weight ethanolic solution. The determination of the APHA color number is carried out firstly directly after work-up of the reaction mixture, in particular after distillation, and after a storage time of the 4-amino-2,2,6,6-tetramethylpiperidine of 30 days and 6 months. The samples are stored at room temperature, under atmospheric pressure and in air atmosphere under normal light conditions.

The starting materials used in the process according to the invention are 2,2,6,6-tetramethylpiperidine-4-one (TAA), ammonia and hydrogen. The ammonia can be introduced into the process according to the invention in liquid form or as an aqueous solution. This aqueous solution of ammonia preferably has a content of ammonia of from 20 to 50% by weight. However, the ammonia is preferably added in liquid form. Catalysts which may be used in the process according to the invention are supported catalysts or skeleton catalysts with the active catalyst metals cobalt and/or nickel. Support materials that may be used for the supported catalysts are, for example, aluminum oxide with a specific surface area of from 100 to 350 $m^2/g$, silicates with a specific surface area of from 400 to 800 $m^2/g$, aluminum silicates with a specific surface area of from 200 to 600 $m^2/g$, kieselguhr with a specific surface area of from 2 to 35 $m^2/g$, activated carbon with a specific surface area of from 800 to 1200 $m^2/g$, nickel oxide or cobalt oxide with a specific surface area of from 400 to 900 $m^2/g$ or zeolites with a specific surface area of from 400 to 900 $m^2/g$. The specific surface area of aluminum oxide includes all values and subvalues therebetween, especially including 150, 200, 250 and 300 $m^2/g$. The specific surface area of silicates includes all values and subvalues therebetween, especially including 450, 500, 550, 600, 650, 700 and 750 $m^2/g$. The specific surface area of aluminum silicates includes all values and subvalues therebetween, especially including 250, 300, 350, 400, 450, 500 and 550 $m^2/g$. The specific surface area of kieselguhr includes all values and subvalues therebetween, especially including 4, 6, 8, 10, 12, 14, 15, 20, 25 and 30 $m^2/g$. The specific surface area of activated carbon includes all values and subvalues therebetween, especially including 850, 900, 950, 1000, 1050, 1100 and 1150 $m^2/g$. The specific surface area of nickel oxide or cobalt oxide includes all values and subvalues therebetween, especially including 450, 500, 550, 600, 650, 700, 750, 800 and 850 $m^2/g$. The specific surface area of zeolites includes all values and subvalues therebetween, especially including 450, 500, 550, 600, 650, 700, 750, 800 and 850 $m^2/g$.

In the process according to the invention, preference is given to using supported catalysts which have from 10 to 60% by weight of the active catalyst metal cobalt and/or nickel. The amount of active catalyst metal cobalt and/or nickel includes all values and subvalues therebetween, especially including 15, 20, 25, 30, 35, 40, 45, 50 and 55% by weight. These supported catalysts are preferably used in the process according to the invention in an amount of from 1 to 15% by weight, preferably from 2 to 12% by weight and particularly preferably from 2.5 to 10% by weight, based on the 2,2,6,6-tetramethylpiperidine-4-one used. The amount of supported catalyst includes all values and subvalues therebetween, especially including 2, 4, 6, 8, 10, 12 and 14% by weight.

Preferably, the skeleton catalysts used in the process according to the invention are skeletal metal catalysts with the active metals cobalt and/or nickel. Such skeletal metal catalyst can be prepared by known methods according to the background art, such as, for example, by a process by M. Raney which is disclosed, for example, in U.S. Pat. No. 1,628,190 or U.S. Pat. No. 1,915,473. In particular, use is made of skeletal metal catalysts for whose production metal alloys have been used which have a content of from 30 to 60% by weight of nickel and/or cobalt and from 70 to 40% by weight of aluminum. The amount of nickel and/or cobalt includes all values and subvalues therebetween, especially including 35, 40, 45, 50 and 55% by weight. The amount of aluminum includes all values and subvalues therebetween, especially including 65, 60, 55, 50 and 45% by weight.

By dissolving out the aluminum, an active catalyst can be produced, the residual aluminum content preferably being in the range from 2 to 20% by weight and preferably in the range from 5 to 10% by weight. The residual aluminum content includes all values and subvalues therebetween, especially including 4, 6, 8, 10, 12, 14, 16 and 18% by weight. The skeletal metal catalyst prepared in this way is preferably used in the process according to the invention in an amount of from 0.5 to 15% by weight, preferably from 1 to 12% by weight and particularly preferably from 1.5 to 10% by weight, based on the 2,2,6,6-tetramethylpiperidine-4-one used. The skeletal metal catalyst is used in amounts which include all values and subvalues therebetween, especially including 1, 1.5, 2, 2.5, 5 and 10% by weight.

The reductive amination in the process according to the invention is carried out in two partial process steps, the main reaction being carried out firstly under relatively mild conditions. At a conversion of 2,2,6,6-tetramethylpiperidine-4-one of at least 80%, preferably at a conversion of at least 90%, pressure and temperature are increased and an after-reaction of the reductive amination carried out. The conversion includes all values and subvalues therebetween, especially including at least 85, 90, 95, 97, 98, 99 and 99.5%. The reaction temperature of the main reaction in the process according to the invention is chosen so that it is lower than the reaction temperature of the after-reaction. Preferably, the main reaction of the process according to the invention is carried out at a temperature of at most 120° C., preferably from 40 to 110° C. and particularly preferably from 45 to 100° C. The reaction temperature of the main reaction includes all values and subvalues therebetween, especially including 50, 60, 70, 80, 90, 100 and 110° C.

The pressure during the main reaction of the process according to the invention is chosen such that this pressure is lower than the pressure during the after-reaction. Here, a pressure of from 5 to 50 bar is advantageous. The pressure includes all values and subvalues therebetween, especially including 10, 15, 20, 25, 30, 35, 40 and 45 bar. When using a catalyst with the active metal nickel, a pressure of from 10 to 30 bar, particularly preferably from 15 to 25 bar, is established. If, however, a catalyst with the active metal cobalt is used in the process according to the invention, then the main reaction is preferably carried out at a pressure of from 15 to 50 bar and particularly preferably from 20 to 45 bar. The pressure required for the process according to the invention is preferably generated exclusively by hydrogen pressure in the process according to the invention.

The solvent used in the process according to the invention is water. The water can firstly be introduced into the reaction mixture as solvent of the ammonia, secondly it may also be added to the reaction mixture as pure substance. By adding the water as pure substance, it is possible to adjust the quantitative ratios of water, ammonia and 2,2,6,6-tetramethylpiperidine-4-one in a targeted manner.

The molar ratio of water to 2,2,6,6-tetramethylpiperidine-4-one in the process according to the invention is preferably from 2:1 to 10:1, preferably from 2.5:1 to 9:1 and particularly preferably from 3:1 to 7:1. Whereas the molar ratio of ammonia to 2,2,6,6-tetramethylpiperidine-4-one is preferably from 1:1 to 5:1, preferably from 1.5:1 to 4:1 and particularly preferably from 2:1 to 3:1 in the process according to the invention.

The after-reaction of the process according to the invention is preferably carried out at temperatures of at least 125° C., preferably at temperatures of from 130° C. to 200° C. and particularly preferably from 140° C. to 180° C. The reaction temperature of the after-reaction includes all values and subvalues therebetween, especially including 130, 135, 140, 145, 150, 155, 160, 165, 170, 175, 180, 185, 190 and 195° C. The pressure during the after-reaction in the process according to the invention is preferably at least 30 bar, preferably from 35 to 150 bar and particularly preferably from 40 to 100 bar. The pressure includes all values and subvalues therebetween, especially including 40, 50, 60, 70, 80, 90, 100, 110, 120, 130 and 140 bar.

The after-reaction is preferably carried out in the same reactor as the main reaction in the process according to the invention. Work-up of the reaction mixture after the main reaction is not necessary before the after-reaction.

After the after-reaction, in the process according to the invention, the reactor is preferably decompressed and the catalyst is firstly separated off from the reaction mixture. The catalyst can be separated off by known methods according to the background art, such as, for example, by filtration. However, in the process according to the invention, preference is given to adding an agglomeration auxiliary, such as, for example, toluene, to the reaction mixture or to the reactor discharge. The addition of the agglomeration auxiliary to the reaction mixture significantly improves the settling behavior of the catalyst in that fine fractions of the catalyst agglomerate and settle considerably more quickly. The catalyst can thus be separated off simply from the liquid phase, preferably by decantation. One advantage of adding even the smallest amounts of an agglomeration auxiliary is the improvement in the settling behavior of the catalyst from the reaction mixture, as a result of which a complex filtration step is saved. It is unimportant here whether this improved sedimentation takes place on account of a reduction in the surface tension, interfacial tension, density, viscosity or another parameter. This simplified removal of the catalyst also offers an advantage in terms of safety since a filtered-off dry cobalt or nickel catalyst is self-igniting. In the process according to the invention, the liquid phase, which comprises the crude product, is preferably decanted off.

In the process according to the invention, the catalyst removed from the reaction mixture can be used in a further reductive amination according to the process according to the invention. In this process, the catalyst is fed to the further reductive amination in the form of a suspension, preferably in the form of a non-self-igniting suspension, particularly preferably in the form of a non-self-igniting aqueous suspension.

Particularly when using catalysts with the active metal cobalt, as well as a recycling of the catalyst, the desired color stability of the 4-amino-2,2,6,6-tetramethylpiperidine is also attained. In order to further improve the color stability, the catalyst can be worked-up following use and before the next use, for example by purification with a suitable solvent, such as, for example, water or lower alcohols, such as ethanol, and a subsequent hydrogen treatment. It would also be conceivable to replace 1 to 30% by weight of the catalyst with fresh catalyst.

In the process according to the invention, the work-up of the liquid phase which comprises the crude product takes place—after separating off the catalyst—preferably through the addition of auxiliaries, such as, for example, alkali metal hydroxides. Thus, the formation of two phases can be improved. Following phase separation, the organic phase can be worked-up by distillation.

In a preferred embodiment of the process according to the invention, an entrainer is added to the liquid phase, the catalyst having already been separated off; the entrainer forms an azeotrope with water, and then an azeotropic distillation is carried out. Of advantage here are entrainers whose azeotrope with water boils below the boiling temperature of the 4-amino-2,2,6,6-tetramethylpiperidine and/or below the boiling temperature of water. Preferably, these are compounds which form a binary azeotrope with water and particularly preferably those which form a binary, heterogeneous azeotrope and thus water can be removed by simple phase separation of the distillate. Entrainers that can be used in the azeotropic distillation are hydrocarbons, such as, for example, hexane, cyclohexane, methylcyclohexane, benzene, toluene, xylene, or alcohols, such as, for example, n-butanol, 2-ethylhexanol, isononanol. It is of course also possible to use all further entrainers known to the person skilled in the art.

The use of an entrainer enables the water which is used as solvent in the reaction and also forms during the reaction to be separated off under mild conditions. As a result, the 4-amino-2,2,6,6-tetramethylpiperidine is less thermally stressed, resulting in better color stability and less coloration of the pure product. After the azeotropic distillation, a distillation of the 4-amino-2,2,6,6-tetramethylpiperidine can follow, preferably under reduced pressure.

Having generally described this invention, a further understanding can be obtained by reference to certain specific examples which are provided herein for purposes of illustration only, and are not intended to be limiting unless otherwise specified.

EXAMPLES

The examples below serve to illustrate the process according to the invention for the preparation of 4-amino-2,2,6,6-tetramethylpiperidine in more detail, without the invention being intended to be limited to this embodiment.

Examples 1-12

300 g of 2,2,6,6-tetramethylpiperidine-4-one, deionized water and 11 g of the catalyst were initially introduced under argon in a 1 l stirred autoclave with a paddle stirrer, electric heating, air cooling and a hydrogen mass through-flow regulator. The catalysts used were firstly B113W (active metal nickel) and secondly B2112Z (active metal cobalt) from Evonik Degussa GmbH. The autoclave was then flushed three times with nitrogen. The stirrer was set at a rotational speed of 300 rpm. Then, 83 g of liquid ammonia were metered in. Then, with the help of hydrogen, the pressure was set at the desired pressure of the main reaction and also the temperature. The after-reaction takes place at a temperature of 150° C. and a pressure of 50 bar for about 3 hours. Conditions for the after-reaction deviating from these were noted in Table 1 below. Table 1 shows both the process parameters, and also the results of the examples carried out.

Examples 13-16

450 g of 2,2,6,6-tetramethylpiperidine-4-one, 250 g of deionized water and 33 g of a cobalt catalyst (type: Evonik Degussa GmbH B2112Z, water-moist) were initially introduced under argon in a 2 l stirred autoclave with blade stirrer and a heated jacket. Then, the autoclave was closed and flushed three times with nitrogen. The stirrer was set to a rotational speed of 500 rpm. Then, 125 g of liquid ammonia were metered in and heated to an internal temperature of 90° C. Then, with the help of hydrogen, a pressure of 40 bar was established. The after-reaction takes place at 150° C. and 50 bar of $H_2$ for about one hour. Cooling was then carried out and the autoclave was decompressed at an internal temperature of about 50° C., flushed twice with nitrogen and the reaction product was discharged under argon.

For work-up, the crude product was stirred at 50° C. and 10 g of toluene were added. This gives a three-phase crude product (lower phase (solid) comprises the cobalt catalyst (solid), middle phase (liquid, pale yellow, slightly cloudy) comprises the desired product; upper phase (liquid): pale yellow-clear toluene phase. The two liquid phases were separated off using a suction tube. The catalyst which remains was admixed with 100 g of deionized water and reused in the next batch. In the following batch, only 150 g of deionized water were then added instead of 250 g of deionized water.

The two liquid phases (805 g, yellowish) were worked-up with a further 140 g of toluene in a distillation apparatus with 10 cm glass column, water separator, reflux condenser and oil bath, in which, at a bottom temperature of at most 130° C. and a top temperature of at most 110° C., an azeotropic distillation was carried out (distillate (water): 312 g and bottom: 580 g). Then, under improved vacuum, the residual toluene was distilled off at a bottom temperature of at most 70° C. and a pressure of 150-30 mbar. 450 g of yellow-colored 4-amino-2,2,6,6-tetramethylpiperidine crude product were retained in the bottom. 130 g of toluene were produced as distillate. After the 4-amino-2,2,6,6-tetramethylpiperidine crude product had been distilled once more overhead (50 cm column; bottom temperature 80-100° C., top temperature 78° C., pressure: 15 mbar), a colorless, storage-stable pure 4-amino-2,2,6,6-tetramethylpiperidine was obtained (see also Table 2).

TABLE 1

| Experiment | Catalyst | Solvent Type | (in g) | Main reaction Pressure ($H_2$, in bar) | Temperature course (in ° C.) | Time (in h) | After-reaction | APHA (20% strength in ethanol) (after . . .) Distillation | 30 days | 6 months | Analysis of the reaction product by means of GC (in area % GC) TAA | TAD | TAA-ol |
|---|---|---|---|---|---|---|---|---|---|---|---|---|---|
| 1 (CE) | Ni | Water | 200 | 20 | 90 | 5 | — | 23 | 98 | 97 | 0 | 95.63 | 1.93 |
| 2 (CE) | Ni | Water | 200 | 20 | 90 | 16 | — | 0 | 7 | 31 | 0 | 93.80 | 2.64 |
| 3 (E) | Ni | Water | 200 | 20 | 90 | 1 | X (p = 70 bar) | 1 (after 4 days) | 4 | 3 | 0 | 93.44 | 2.98 |
| 4 (E) | Ni | Water | 222 | 40 | 55-100 | 3 | X | 2 | 0 | 1 | 0 | 90.73 | 6.54 |
| 5 (E) | Ni | Water | 111 | 40 | 55-100 | 3 | X | 7 | 13 | 12 | 0 | 92.10 | 5.49 |
| 6 (E) | Ni | Water | 111 | 20 | 55-100 | 3 | X | 2 | 5 | 3 | 0 | 92.49 | 4.65 |
| 7 (E) | Co | Water | 111 | 40 | 80-100 | 4 | X | 3 | 5 | 4 | 0 | 94.27 | 2.38 |
| 8 (CE) | Co | Methanol | 111 | 40 | 100-120 | 3 | X | 43 | 29 | 20 | 0 | 94.86 | 1.27 |
| 9 (E) | Co | Water | 111 | 20 | 90-120 | 3 | X | 1 | 2 | 3 | 0 | 85.05 | 2.89 |
| 10 (E) | Co | Water | 111 | 40 | 90-130 | 3 | X | 1 | 2 | 2 | 0 | 94.07 | 2.53 |
| 11 (E) | Co (from 10) | Water | 111 | 40 | 90-130 | 3 | X | 2 | 7 | 10 | 0 | 92.32 | 3.50 |
| 12 (E) | Co (from 11) | Water | 111 | 40 | 100-130 | 4 | X | 9 | 8 | 8 | 0 | 91.95 | 2.82 |

E: example according to the invention
CE: comparative example

TABLE 2

| Experiment | Catalyst | Solvent Type | (in g) | Main reaction Pressure ($H_2$, in bar) | Temperature course (in ° C.) | Time (in h) | After-reaction | APHA (20% strength in ethanol) (after . . .) Distillation | 30 days | 6 months | Analysis of the reaction product by means of GC (in area % GC) TAA | TAD | TAA-ol |
|---|---|---|---|---|---|---|---|---|---|---|---|---|---|
| 13 (E) | Co | Water | 250 | 40 | 90-120 | 4 | X | 0 | 3 | 2 | 0 | 94.54 | 3.90 |
| 14 (E) | Co (from 13) | Water | 250 | 40 | 90-120 | 5 | X | 1 | 3 | 14 | 0 | 91.78 | 3.76 |
| 15 (E) | Co (from 14) | Water | 250 | 40 | 90-120 | 4 | X | 3 | 3 | 2 | 0 | 92.93 | 3.76 |
| 16 (E) | Co (from 15) | Water | 250 | 40 | 100-120 | 4 | X | 4 | 4 | 8 | 0 | 93.32 | 3.15 |

German patent applications DE 10 2008 000214.3 filed Feb. 1, 2008 and DE 10 2008 040045.9, filed Jul. 1, 2008, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for the preparation of 4-amino-2,2,6,6-tetramethylpiperidine, comprising:
   (1) reacting, in a main reaction, 2,2,6,6-tetramethylpiperidine-4-one with ammonia and hydrogen in the presence of a nickel and/or cobalt catalyst, and water,
   at a pressure of at most 50 bar and a temperature of at most 120° C. up to a conversion of the 2,2,6,6-tetramethylpiperidine-4-one of at least 80%, to obtain a reaction mixture, and
   (2) then after-reacting said reaction mixture at a higher temperature and at a higher pressure compared to the pressure and temperature of the main reaction.

2. The process according to claim 1, wherein water and 2,2,6,6-tetramethylpiperidine-4-one are used in a molar ratio of from 2.5:1 to 9:1.

3. The process according to claim 1, wherein water and 2,2,6,6-tetramethylpiperidine-4-one are used in a molar ratio of from 3:1 to 7:1.

4. The process according to claim 1, wherein said catalyst is a skeletal metal catalyst in which an active metal is cobalt and/or nickel.

5. The process according to claim 4, wherein from 0.5 to 15% by weight of the skeletal metal catalyst are used, based on a total amount of 2,2,6,6-tetramethylpiperidine-4-one.

6. The process according to claim 1, wherein the main reaction is carried out at a temperature of from 40 to 110° C.

7. The process according to claim 1, wherein the main reaction is carried out at a pressure of from 5 to 50 bar.

8. The process according to claim 1, wherein the after-reaction is carried out at a temperature of from 130 to 200° C.

9. The process according to claim 1, wherein the after-reaction is carried out at a pressure of from 35 to 150 bar.

10. The process according to claim 1, wherein the after-reaction is carried out in the same reactor as the main reaction.

11. The process according to claim 1, wherein no work-up of the reaction mixture after the main reaction and before the after-reaction takes place.

12. The process according to claim 1, wherein ammonia and 2,2,6,6-tetramethylpiperidine-4-one are used in a molar ratio of from 1.5:1 to 4:1.

13. The process according to claim 1, wherein the catalyst is separated off from a liquid phase of said reaction mixture by decantation, an agglomeration auxiliary being added beforehand to the reaction mixture.

14. The process according to claim 13, wherein the separated off catalyst is fed as suspension to a second reductive amination of 2,2,6,6-tetramethylpiperidine-4-one with ammonia and hydrogen in the presence of a nickel and/or cobalt catalyst, and water,
   wherein a main reaction is carried out at a pressure of at most 50 bar and a temperature of at most 120° C. up to a conversion of the 2,2,6,6-tetramethylpiperidine-4-one of at least 80%, and then an after-reaction takes place at a higher temperature and at a higher pressure compared to the pressure and temperature of the main reaction.

15. The process according to claim 13, wherein an entrainer is added to the liquid phase after the catalyst has been separated off and then an azeotrope distillation is carried out to separate off the water which has been used in the reaction as a solvent.

16. The process according to claim 15, followed by distillation of the 4-amino-2,2,6,6-tetramethylpiperidine.

17. The process according to claim 1, wherein said 4-amino-2,2,6,6-tetramethylpiperidine has a APHA color number of <20 for a storage time of 6 month.

18. A process for the preparation of 4-amino-2,2,6,6-tetramethylpiperidine, comprising:
   (1) reacting, in a main reaction, 2,2,6,6-tetramethylpiperidine-4-one with ammonia and hydrogen in the presence of a nickel and/or cobalt catalyst, and water,
   at a pressure of at most 50 bar and a temperature of at most 120° C. up to a conversion of the 2,2,6,6-tetramethylpiperidine-4-one of at least 80%, to obtain a reaction mixture, and
   (2) then after-reacting said reaction mixture at a higher temperature and at a higher pressure compared to the pressure and temperature of the main reaction,
   wherein water and 2,2,6,6-tetramethylpiperidine-4-one are used in a molar ratio of from 2.5:1 to 9:1, and
   wherein said 4-amino-2,2,6,6-tetramethylpiperidine has a APHA color number of <20 for a storage time of 6 month.

19. A process for the preparation of 4-amino-2,2,6,6-tetramethylpiperidine, comprising:
   (1) reacting, in a main reaction, 2,2,6,6-tetramethylpiperidine-4-one with ammonia and hydrogen in the presence of a nickel and/or cobalt catalyst, and water,
   at a pressure of at most 50 bar and a temperature of at most 120° C. up to a conversion of the 2,2,6,6-tetramethylpiperidine-4-one of at least 80%, to obtain a reaction mixture, and
   (2) then after-reacting said reaction mixture at a higher temperature and at a higher pressure compared to the pressure and temperature of the main reaction,
   wherein water and 2,2,6,6-tetramethylpiperidine-4-one are used in a molar ratio of from 2.5:1 to 9:1.

20. A process for the preparation of 4-amino-2,2,6,6-tetramethylpiperidine, comprising:
   (1) reacting, in a main reaction, 2,2,6,6-tetramethylpiperidine-4-one with ammonia and hydrogen in the presence of a nickel and/or cobalt catalyst, and water,
   at a pressure of at most 50 bar and a temperature of at most 120° C. up to a conversion of the 2,2,6,6-tetramethylpiperidine-4-one of at least 80%, to obtain a reaction mixture, and
   (2) then after-reacting said reaction mixture at a higher temperature and at a higher pressure compared to the pressure and temperature of the main reaction;
   wherein the after-reaction is carried out at a temperature of from 130 to 200° C. and at a pressure of from 35 to 150 bar.

* * * * *